United States Patent [19]
Cai et al.

[11] Patent Number: 6,103,903
[45] Date of Patent: Aug. 15, 2000

[54] 4-(4-PIPERIDYLMETHYHLAMINO) SUBSTITUTED HETEROARYL FUSED PYRIDINES: GABA BRAIN RECEPTOR LIGANDS

[75] Inventors: Guolin Cai, Guilford, Conn.; Gang Liu, Agoura, Calif.

[73] Assignee: Neurogen Corporation, Branford, Conn.

[21] Appl. No.: 09/259,150

[22] Filed: Feb. 26, 1999

Related U.S. Application Data

[60] Provisional application No. 60/076,006, Feb. 26, 1998.

[51] Int. Cl.[7] ..................... C07D 471/04; C07D 495/04; C07D 401/14; C07D 409/14
[52] U.S. Cl. .......................... 546/114; 546/122; 544/236; 544/279; 544/350
[58] Field of Search .................................... 546/114, 122; 544/236, 279, 350

[56] References Cited

U.S. PATENT DOCUMENTS

| | | | |
|---|---|---|---|
| 4,935,431 | 6/1990 | Ife | 514/301 |
| 5,026,700 | 6/1991 | Harrison | 514/233.8 |
| 5,243,049 | 9/1993 | Shaw et al. | 546/84 |

FOREIGN PATENT DOCUMENTS

| | | |
|---|---|---|
| 1 177 849 | 1/1970 | United Kingdom . |
| 1-177849 | 1/1970 | United Kingdom . |
| WO 95/11885 | 5/1995 | WIPO . |
| WO 98/02420 | 1/1998 | WIPO . |
| WO 9802433 | 1/1998 | WIPO . |
| WO 99/43681 | 9/1999 | WIPO . |

OTHER PUBLICATIONS

Luisa Savini et al., Il Farmaco, vol. 48, No. 1, 1993, pp. 65–75.
Christopher D. Benham et al., Bioorganic and Medicinal Chemistry Letters, vol. 5, No. 21, 1995, pp. 2455–2460.
T. P. Blackburn et al., Bioorganic and Medicinal Chemistry Letters, vol. 5, No. 22, 1995, pp. 2589–2592.

*Primary Examiner*—Evelyn Mei Huang
*Attorney, Agent, or Firm*—McDonnell Boehnen Hulbert & Berghoff; Steven J. Sarussi

[57] ABSTRACT

Disclosed are compounds of the formula

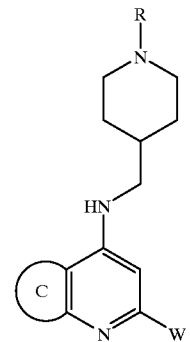

or the pharmaceutically acceptable non-toxic salts thereof wherein:

R is hydrogen, alkyl, or(un)substituted alkoxy or amino; and

W is (un)substituted alkyl, aryl, or heteroaryl, which compounds are highly selective agonists, antagonists or inverse agonists for GABAa brain receptors or prodrugs of agonists, antagonists or inverse agonists for GABAa brain receptors. The compounds of the invention are useful in the diagnosis and treatment of anxiety, Down Syndrome, sleep, cognitive and seizure disorders, and overdose with benzodiazepine drugs and for enhancement of alertness.

19 Claims, No Drawings

4-(4-PIPERIDYLMETHYHLAMINO) SUBSTITUTED HETEROARYL FUSED PYRIDINES: GABA BRAIN RECEPTOR LIGANDS

This is a continuation-in-part of provisional application Ser. No. 60/076,006, filed Feb. 26, 1998.

BACKGROUND OF THE INVENTION

1. Field of the Invention

This invention relates to certain heterocyclic amino substituted heteroaryl fused pyridines which selectively bind to GABAa receptors. This invention also relates to pharmaceutical compositions comprising such compounds. It further relates to the use of such compounds in treating anxiety, sleep and seizure disorders, and overdoses of benzodiazepine-type drugs, and enhancing alertness. The interaction of heterocyclic amino substituted heteroaryl fused pyridines of the invention with a GABA binding site, the benzodiazepines (BDZ) receptor, is described. This interaction results in the pharmacological activities of these compounds.

2. Description of the Related Art

γ-Aminobutyric acid (GABA) is regarded as one of the major inhibitory amino acid transmitters in the mammalian brain. Over 40 years have elapsed since its presence in the brain was demonstrated (Roberts & Frankel, J. Biol. Chem 187: 55–63, 1950; Udenfriend, J. Biol. Chem. 187: 65–69, 1950). Since that time, an enormous amount of effort has been devoted to implicating GABA in the etiology of seizure disorders, sleep, anxiety and cognition (Tallman and Gallager, Ann. Rev. Neuroscience 8: 21–44, 1985). Widely, although unequally, distributed through the mammalian brain, GABA is said to be a transmitter at approximately 30% of the synapses in the brain. GABA mediates many of its actions through a complex of proteins localized both on cell bodies and nerve endings; these are called GABAa receptors. Postsynaptic responses to GABA are mediated through alterations in chloride conductance that generally, although not invariably, lead to hyperpolarization of the cell. Drugs that interact at the GABAa receptor can possess a spectrum of pharmacological activities depending on their abilities to modify the actions of GABA.

The 1,4-Benzodiazepines, such as diazepam, continue to be among the most widely used drugs in the world as anxiolytics, sedative-hypnotics, muscle relaxants, and anti-convulsants. A number of these compounds are extremely potent drugs; such potency indicates a site of action with a high affinity and specificity for individual receptors. Early electrophysiological studies indicated that a major action of benzodiazepines was enhancement of GABAergic inhibition. Presently, those compounds possessing activity similar to the benzodiazepines are called agonists. Compounds possessing activity opposite to benzodiazepines are called inverse agonists, and the compounds blocking both types of activity have been termed antagonists.

The GABAa receptor subunits have been cloned from bovine and human cDNA libraries (Schoenfield et al., 1988; Duman et al., 1989). A number of distinct cDNAs were identified as subunits of the GABAa receptor complex by cloning and expression. These are categorized into α, β, γ, δ, ε, and provide a molecular basis for the GABAa receptor heterogeneity and distinctive regional pharmacology (Shivvers et al., 1980; Levitan et al., 1989). The γ subunit appears to enable drugs like benzodiazepines to modify the GABA responses (Pritchett et al., 1989). The presence of low Hill coefficients in the binding of ligands to the GABAa receptor indicates unique profiles of subtype specific pharmacological action.

With the discovery of the "receptor" for the benzodiazepines and the subsequent definition of the nature of the interaction between GABA and the benzodiazepines, it appears that the behaviorally important interactions of the benzodiazepines with different neurotransmitter systems are due in a large part to the enhanced ability of GABA itself to modify these systems. Each modified system, in turn, may be associated with the expression of a behavior. Depending on the mode of interaction, these compounds are capable of producing a spectrum of activities (either sedative, anxiolytic, and anticonvulsant, or wakefulness, seizures, and anxiety).

SUMMARY OF THE INVENTION

This invention provides novel compounds of Formula I which interact with a GABAa binding site, the benzodiazepine receptor.

The invention provides pharmaceutical compositions comprising compounds of Formula I. The invention also provides compounds useful in the diagnosis and treatment of anxiety, sleep and seizure disorders, overdose with benzodiazepine drugs and for enhancement of memory. Accordingly, a broad embodiment of the invention is directed to compounds of general Formula I:

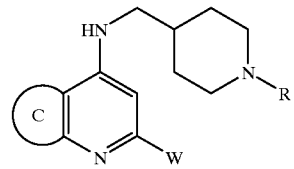

I wherein:

the C ring represents a thiophene, pyridine, pyrazine, pyridazine, or pyrimidine ring, each of which is optionally substituted independently with one or two groups selected from $C_1$–$C_6$ alkoxy, $C_1$–$C_6$ alkoxy, halogen, hydroxy, amino, mono- or di($C_1$–$C_6$)alkyl amino, or trifluoromethyl;

W is aryl, heteroaryl, 2- or 3-thienyl, or 2-, 3-, or 4-pyridyl, each of which may be mono, di- or trisubstituted independently with halogen, hydroxyl, lower alkyl, lower alkoxy, amino, or mono- or dialkylamino where each alkyl portion is lower alkyl; or $CONR_4R_5$ wherein $R_4$ and $R_5$ are the same or different and represent lower alkyl; and R represents hydrogen, lower alkyl, hydroxy($C_1$–$C_6$) alkyl, amino($C_1$–$C_6$)alkyl, mono- or di($C_1$–$C_6$) alkylamino($C_1$–$C_6$)alkyl, alkoxy ($C_1$–$C_6$) alkyl, ($C_1$–$C_6$) alkoxy, or aryl ($C_1$–$C_6$) alkyl; or R represents $CONR_1R_2$ where $R_1$ and $R_2$ are the same or different and represent, hydrogen or lower alkyl or NR, $R_2$ forms a ring having from 3–7, preferably 5–6, members.

These compounds are highly selective agonists, antagonists or inverse agonists for GABAa brain receptors or prodrugs of agonists, antagonists or inverse agonists for GABAa brain receptors. In other words, while the compounds of the invention all interact with GABAa brain receptors, they do not display identical physiological activity. Thus, these compounds are useful in the diagnosis and treatment of anxiety, sleep and seizure disorders, overdose with benzodiazepine drugs and for enhancement of memory. For example, these compounds can be used to treat overdoses of benzodiazepine-type drugs as they would competitively bind to the benzodiazepine receptor.

DETAILED DESCRIPTION OF THE INVENTION

The novel compounds encompassed by the instant invention can be described by general Formula I set forth above or the pharmaceutically acceptable non-toxic salts thereof.

In addition, the present invention also encompasses compounds of Formula IIa and IIb

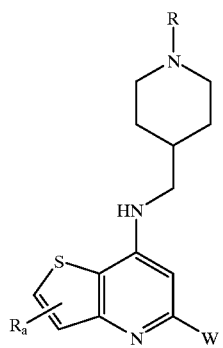

IIa

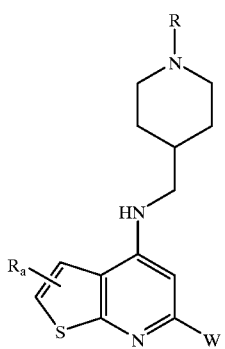

IIb or the pharmaceutically acceptable non-toxic salts thereof wherein W and R are as defined above for Formula I; and $R_a$ is hydrogen, $C_1$–$C_6$ alkoxy, $C_1$–$C_6$ alkoxy, halogen, hydroxy, amino, mono- or di($C_1$–$C_6$)alkyl amino, or trifluoromethyl.

Preferred compounds of Formula IIa and IIb are where W is aryl or heteroaryl mono or disubstituted independently with halogen, hydroxyl, lower alkyl, or lower alkoxy.

Other preferred compounds of Formula IIa and IIb are where R is hydrogen, lower alkyl.

Preferred $R_a$ groups include $C_1$–$C_3$ alkyl, $C_1$–$C_3$ alkoxy, hydroxy, dimethyl amino, diethylamino, ethylamino, chloro, fluoro and bromo. Particularly preferred $R_a$ groups are chloro, bromo, fluoro, methylethyl and amino.

The present invention also encompasses compounds of Formula III:

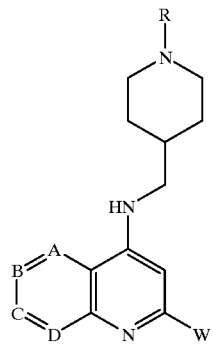

III wherein W and R are as defined above for Formula I; and

A, B, C, and D are independently $CR_3$, or nitrogen, provided that no more than two of A, B, C, and D are nitrogen simultaneously;

$R_3$ is hydrogen, alkyl, halogen, hydroxy, or lower alkoxy.

Other preferred compounds of the invention are encompassed by the following formulae:

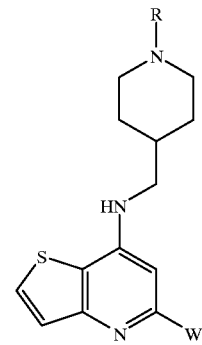

IV where

R is as defined above for Formula I; and

W is aryl or 2-, 3-, or 4-pyridyl, each of which may be mono or disubstituted independently with halogen, lower alkyl, lower alkoxy, amino, or mono- or dialkylamino where each alky portion is lower alkyl, or $CONR_4R_5$ wherein $R_4$ and $R_5$ are same or different and represent lower alkyl.

More preferred compounds of Formula IV are those where W is

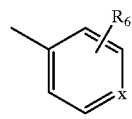

wherein $R_6$ is halogen, hydroxy, lower alkyl, lower alkoxy, amino, or mono- or dialkylamino where each alkyl portion is lower alkyl, or $R_6$ is $CONR_4R_5$ wherein $R_7$ and $R_8$ are the same or different and represent lower alkyl; and X is $CR_9$ or nitrogen, where $R_9$ is hydrogen, lower alkyl, halogen, hydroxy, or lower alkoxy.

Even more preferred compounds of Formula IV are those where R is hydrogen, $R_6$ is hydrogen or lower alkoxy, and X is $CR_9$ or nitrogen, where $R_9$ is hydrogen, fluorine, methoxy, or ethoxy.

The present invention also encompassess compounds of Formula V:

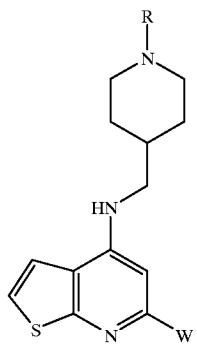

where

R is as defined above for Formula I; and

W is aryl or 2-, 3-, or 4-pyridyl, each of which may be mono or disubstituted independently with halogen, lower alkyl, lower alkoxy, amino, or mono- or dialkylamino where each alkyl portion is lower alkyl, or $CONR_4R_5$ where $R_4$ and $R_5$ are same or different and represent lower alkyl.

More preferred compounds of Formula V are those where W is

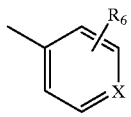

wherein $R_6$ is halogen, hydroxy, lower alkyl, lower alkoxy, amino, or mono- or dialkylamino where each alkyl portion is lower alkyl, or $CONR_7R_8$ wherein $R_7$ and $R_8$ are the same or different and represent lower alkyl; and X is $CR_9$ or nitrogen, where $R_9$ is hydrogen, lower alkyl, halogen, hydroxy, or lower alkoxy.

Even more preferred compounds of Formula V are those where R is hydrogen, $R_6$ is hydrogen or lower alkoxy, and X is $CR_9$ or nitrogen, where $R_9$ is hydrogen, fluorine, methoxy, or ethoxy.

The present invention also encompassess compounds of Formula VI:

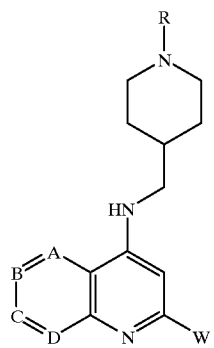

where

A, B, C, and D are $CR_3$, or nitrogen, provided that no more than two of A, B, C, and D are nitrogen simultaneously;

$R_3$ is hydrogen, lower alkyl, halogen, hydroxy, or lower alkoxy;

R is as defined above for Formula I; and

W is aryl or 2-, 3-, or 4-pyridyl, each of which may be mono or disubstituted independently with halogen, hydroxy, lower alkyl, lower alkoxy, amino, or mono- or dialkylamino where each alkyl portion is lower alkyl, or $CONR_4R_5$ wherein $R_4$ and $R_5$ are same or different and representing lower alkyl.

More preferred compounds of Formula VI are those where W is

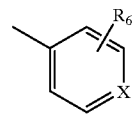

wherein $R_6$ is halogen, hydroxy, lower alkyl, lower alkoxy, amino, mono- or dialkylamino where each alkyl portion is lower alkyl, or $CONR_7R_8$ wherein $R_7$ and $R_8$ are the same or different and represent lower alkyl; and X is $CR_9$ or nitrogen, and $R_9$ is hydrogen, lower alkyl, halogen, hydroxy, or lower alkoxy.

Even more preferred compounds of Formula VI are those where A is nitrogen, B, C, and D are hydrogen, R is hydrogen, $R_2$ is hydrogen, and X is $CR_1$, where $R_1$ is hydrogen, fluorine, methoxy or ethoxy.

Representative compounds of the present invention, which are encompassed by Formula I, include, but are not limited to the compounds in Table I and their pharmaceutically acceptable acid and base addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)n—COOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By "alkyl" and "lower alkyl" in the present invention is meant straight or branched chain alkyl groups having 1–6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "alkoxy" and "lower alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy pentoxy, 2-pentyl, isopentoxy, neopentoxy, hexoxy, 2-hexoxy, 3-hexoxy, and 3-methylpentoxy.

By the term "halogen" in the present invention is meant fluorine, bromine, chlorine, and iodine.

By heteroaryl is meant one or more aromatic ring systems of 5-, 6-, or 7-membered rings containing at least one and up to four heteroatoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, napthyridinyl, benzimidazolyl, benzoxazolyl.

By aryl is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, lower alkyl, lower alkoxy, lower alkylthio, trifluoromethyl, lower acyloxy, aryl, heteroaryl, and hydroxy.

Representative compounds of the invention are shown below in Table 1.

TABLE 1

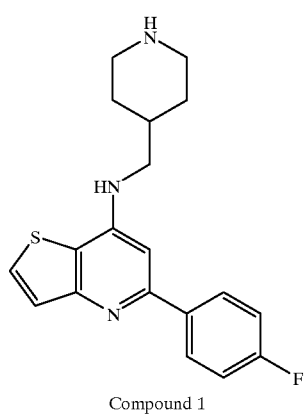

Compound 1

TABLE 1-continued

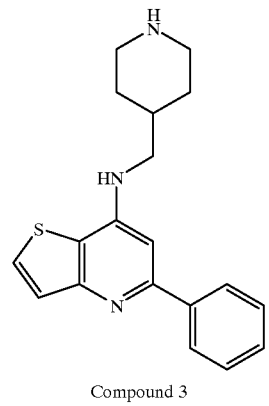

Compound 3

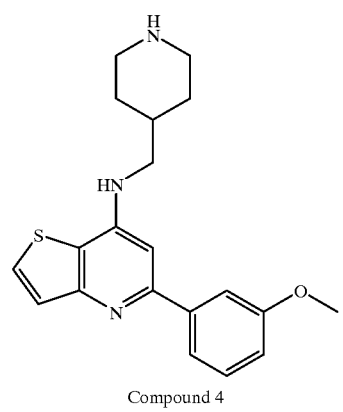

Compound 4

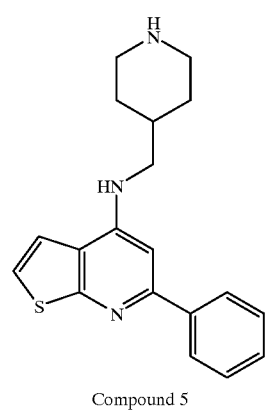

Compound 5

TABLE 1-continued

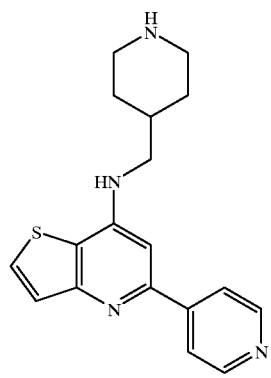

Compound 6

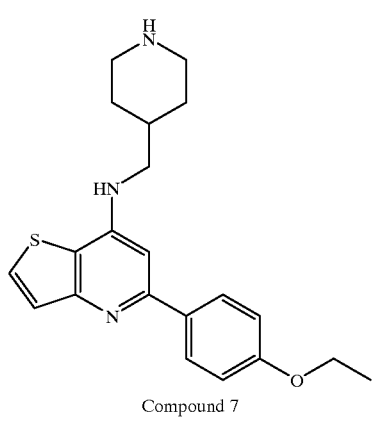

Compound 7

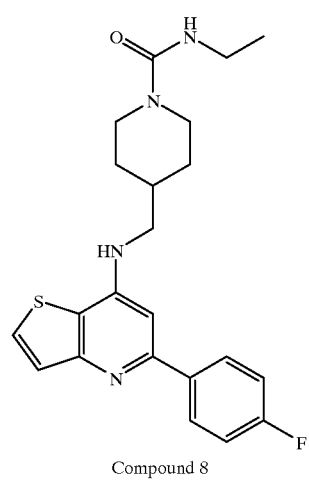

Compound 8

TABLE 1-continued

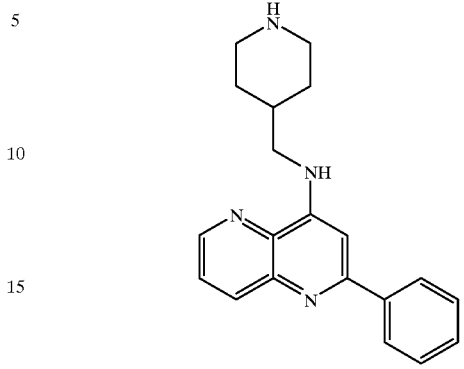

Compound 9

The pharmaceutical utility of compounds of this invention is indicated by the assays for GABAa receptor binding activity set forth in the Examples below.

The compounds of Formula I and their salts are suitable for the diagnosis and treatment of anxiety, Down Syndrome, sleep, cognitive and seizure disorders, and overdose with benzodiazepine drugs and for enhancement of alertness, both in human and non-human animals and domestic pets, especially dogs and cats and farm animals such as sheep, swine and cattle.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It will be convenient to formulate these animal feed and drinking water compositions with a mullet-dose of the drug so that the animal takes in an appropriate quantity of the composition along with its diet. It will also be convenient to present the composition as a premix for addition to the feed or drinking water.

An illustration of the preparation of compounds of the present invention is given in Schemes I.

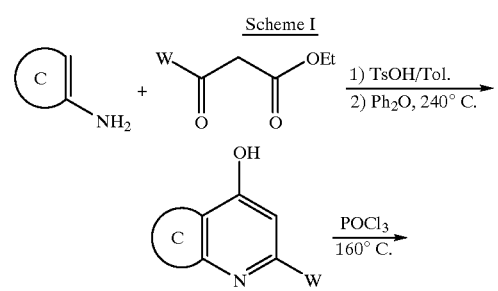

-continued

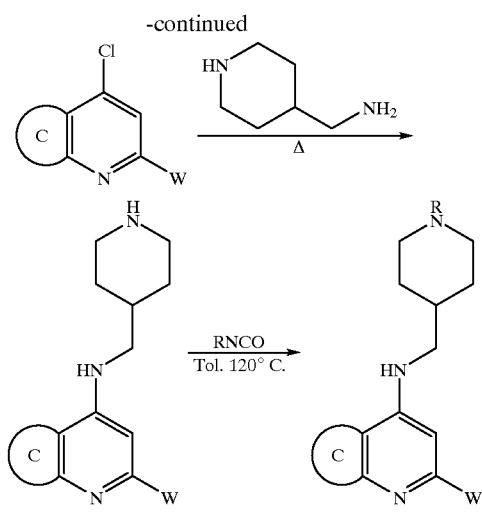

In the above scheme, the W and C rings are as defined above for Formula I.

An illustration of the preparation of compounds of the present invention is given in Scheme I. Those having skill in the art will recognize that the starting materials may be varied and additional steps employed to produce compounds encompassed by the present invention, as demonstrated by the following examples.

As shown, an aniline is reacted with a β-keto ester in the presence of an acid, such as, for example, P-toluenesulfonic acid, to form a 4-hydroxypyridine which is subsequently converted to the 4-chloropyridine upon treatment with a nucleophilic halogenating reagent such phosphorus oxychloride. The resulting chloride is reacted with 4-(Aminomethyl)piperdine at elevated temperatures to form the N-alkylated product. The piperidine can then be further derivatized with a desired isocyanate, such as, for example, methyl isocyanate, to form the target compound.

The disclosures in this application of all articles and references, including patents, are incorporated herein by reference.

The invention is illustrated further by the following examples which are not to be construed as limiting the invention in scope or spirit to the specific procedures described in them.

The starting materials and various intermediates may be obtained from commercial sources, prepared from commercially available organic compounds, or prepared using well known synthetic methods.

Representative examples of methods for preparing intermediates of the invention are set forth below.

EXAMPLE 1

1. 5-(4-Fluorophenyl)-thieno[3,2-b]pyridin-7-ol

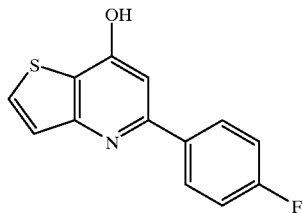

A mixture of 3-amino-2-thiophenecarboxylic acid (8 g, 49 mmol), ethyl 4-fluorobenzoylacetate (9.6 g, 49 mmol), and p-toluenesulfonic acid monohydrate (0.2 g, 1 mmol) in toluene (100 mL) is refluxed for 20 hours with a Dean-Stark water trap to remove produced water. After cooling to room temperature, the precipitate is filtered and washed with diethyl ether. The solid is dissolved in diphenyl ether (80 mL) and heated at 220° C. for 2 hours. The reaction solution is then cooled to room temperature, diethyl ether is added, and the precipitate is filtered and washed with diethyl ether to give 5-(4-fluorophenyl)-thieno[3,2-b]pyridin-7-ol (2 g, 17% yield) as brown crystalline needles, m.p. 316–318°C.

2. 7-Chloro-5-(4-fluorophenyl)thieno[3,2-b]pyridine

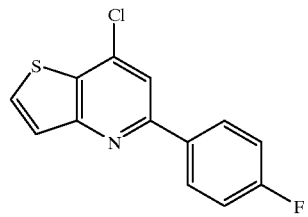

A solution of 5-(4-fluorophenyl)-thieno[3,2-b]pyridin-7-ol (1.6 g) in phosphorus oxychloride (50 mL) is refluxed for 3 hours. After the excess amount of phosphorus oxychloride is removed under vacuum, the residue is treated with ethyl acetate (20 mL), and NaOH (2N, 20 mL). The mixture is extracted with ethyl acetate (3×20 mL). The combinded organic layers are washed with brine and dried over $MgSO_4$. Evaporation of the solvent affords 7-chloro-5-(4-fluorophenyl)thieno[3,2-b]pyridine (1.5 g, 88% yield) as a white solid, m.p. 119–121°C.

3. N-(4-piperidinylmethyl)-5-(4-fluorophenyl) thieno [3,2-b]pyridin-7-amine

A solution of 7-chloro-5-(4-fluorophenyl)thieno[3,2-b] pyridine (60 mg, 0.23 mmole) in 4-aminomethylpiperidine (1 mL) is heated at 160°C. oil bath under $N_2$ for 4 hours. The reaction mixture is cooled to room temperature and purified on preperative tlc plate to give N-(4-piperidinylmethyl)-5-(4-fluorophenyl)thieno[3,2-b]pyridin-7-amine (15 mg, 19% yield) as a colorless oil. This material is dissolved in 1 mL ethyl acetate. Ethyl acetate saturated with HCl (2 mL) is added and then concentrated to afford N-(4-piperidinylmethyl)-5-(4-fluorophenyl)thieno[3,2-b]pyridin-7-amine dihydrochloride (compound 1) as a greasy oil. The salt is triturated with ether, collected by filtration, washed with ether and dried in vacuo, m.p. >260° C. (dec).

EXAMPLE 2

4-Chloro-6-phenylthieno[2,3-b]pyridine

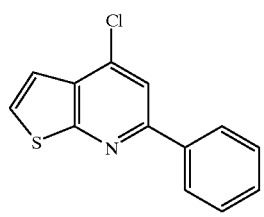

A mixture of 3-aminothiophene (4 g, 0.04 mole), ethyl benzoylacetate (11 mL, 0.06 mole), toluene (100 mL), and p-toluene sulfonic acid monohydrate (300 mg) is stirred and heated under reflux with a Dean-Stark water trap at 120°C. for 16 hours. The reaction mixture is concentrated, and diphenyl ether (30 mL) is added. After heating at 240°C. for 1 hour, the reaction mixture was allowed to cool to room temperature. The reaction mixture is diluted with hexane, and the semi-solid collected is then purified by short silica gel column ($CH_2Cl_2$/MeOH/$NH_4OH$: 10:1:0.1). The resulting product, 4-hydroxy-6-phenyl-thieno[2,3-b]pyridine, is treated with phosphorus oxychloride (30 mL) and heated under reflux for 3 hours. This mixture is cooled to room temperature, poured onto ice, neutralized with 10 N sodium hydyoxide, and extracted with methylene chloride (3×20 mL). The combined organic layers are dried over sodium sulfate, concentrated in vacuo. and the residue is purified by chromatography to give 4-chloro-6-phenylthieno[2,3-b]pyridine as a yellowish solid (1.1 g, 11% total yield), m.p. 83–85°C.

EXAMPLE 3

N-(4-N-ethylcarboxamidepiperidinylmethyl)-5-(4-fluorophenyl)thieno[3,2-b]pyridin-7-amine Compound 2

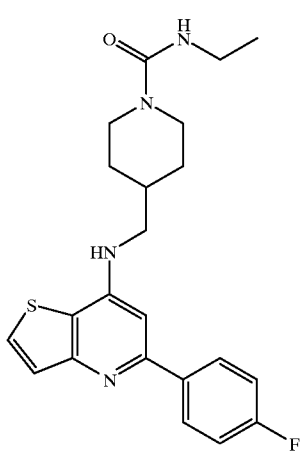

A reaction solution of N-(4-piperidinylmethyl)-5-(4-fluorophenyl)thieno[3,2-b]pyridin-7-amine (10 mg, 0.03 mmole), ethyl isocyanate (0.1 mL) in toluene (5 mL) is heated at 120°C. oil bath for 1 hour. The resulting solution is cooled down to room temperature and concentrated. The residue is purified on a preparative tlc plate to give N-(4-N-ethylcarboxamidepiperidinylmethyl)-5-(4-fluorophenyl) thieno[3,2-b]pyridin-7-amine (1 mg, 8% yield) as a colorless oil. This material is dissolved in 1 mL ethyl acetate. Ethyl acetate saturated with HCl (2 mL) is added and then concentrated to afford N-(4-N-ethylcarboxamidepiperidinylmethyl)-5-(4-fluorophenyl) thieno[3,2-b]pyridin-7-amine hydrochloride (compound 2) as a greasy oil. The salt was solidified with ether.

EXAMPLE 4

The following compounds are prepared essentially according to the procedure described in Examples 1–5:
 a) N-(4-Piperidinylmethyl)-5-phenylthieno[3,2-b] pyridin-7-amine dihydrochloride (compound 3).
 b) N-(4-Piperidinylmethyl)-5-(3-methoxyphenyl)thieno [3,2-b]pyridin-7-amine dihydrochloride (compound 4).
 c) N-(4-Piperidinylmethyl)-6-phenylthieno[2,3-b] pyridin-4-amine dihydrochloride (compound 5).
 d) N-(4-Piperidinylmethyl)-5-(4-pyridinyl)thieno[3,2-b] pyridin-7-amine dihydrochloride (compound 6).
 e) N-(4-Piperidinylmethyl)-5-(4-ethoxyphenyl)thieno[3,2-b]pyridin-7-amine dihydrochloride (compound 7).
 f) N-(4-N-Ethylcarboxamidepiperidinylmethyl)-5-(4-fluorophenyl)thieno[3,2-b]pyridin-7-amine hydrochloride (compound 8).
 g) 4-(4-Piperidinylmethylamino)-2-phenyl-1,5-naphthyridine. (compound 9).

EXAMPLE 5

The pharmaceutical utility of compounds of this invention is indicated by the following assay for GABAa receptor binding activity.

Assays are carried out as described in Thomas and Tallman (*J. Bio. Chem.* 156: 9838–9842 , *J. Neurosci.* 3: 433–440, 1983). Rat cortical tissue is dissected and homogenized in 25 volumes (w/v) of 0.05 M Tris HCl buffer (pH 7.4 at 4° C.). The tissue homogenate is centrifuged in the cold (4°) at 20,000×g for 20'. The supernatant is decanted and the pellet is rehomogenized in the same volume of buffer and again centrifuged at 20,000×g. The supernatant is decanted and the pellet is frozen at –20° C. overnight. The pellet is then thawed and rehomogenized in 25 volume (original wt/vol) of buffer and the procedure is carried out twice. The pellet is finally resuspended in 50 volumes (w/vol of 0.05M Tris HCl buffer (pH 7.4 at 40° C.).

Incubations contain 100ml of tissue homogenate, 100ml of radioligand 0.5nM ($^3$H-RO15-1788 [$^3$H-Flumazenil] specific activity 80 Ci/mmol), drug or blocker and buffer to a total volume of 500 ml. Incubations are carried for 30min at 4° C. then are rapidly filtered through GFB filters to separate free and bound ligand. Filters are washed twice with fresh 0.05M Tris HCl buffer (pH 7.4 at 4° C.) and counted in a liquid scintillation counter. 1.0mM diazepam is added to some tubes to determine nonspecific binding. Data are collected in triplicate determinations, averaged and % inhibition of total specific binding is calculated. Total Specific Binding=Total–Nonspecific. In some cases, the amounts of unlabeled drugs is varied and total displacement curves of binding are carried out. Data are converted to $IC_{50}$ or $K_i$. The Ki values for the compounds in this invention are less than 200 nM.

EXAMPLE 6

In addition, the following assay may be used to determine if the compounds of the invention are agonists, antagonists, or inverse agonists, and, therefore, their specific pharmaceutical utility. The following assay can be employed to determine specific GABAa receptor activity.

Assays are carried out as described in White and Gurley (NeuroReport 6: 1313–1316, 1995) and White, Gurley, Hartnett, Stirling, and Gregory (Receptors and Channels 3: 1–5, 1995) with modifications. Xenopus Laevis oocytes are enzymatically isolated and injected with non-polyadenylated cRNA mixed in a ratio of 4:1:4 for human derived α, β, and γ subunits, respectively. For each subunit combination, sufficient message is injected to result in current amplitudes of >10 nA when 1 μM GABA is applied.

Electrophysiological recordings are carried out using the two electrode voltage-clamp technique at a membrane holding potential of –70 mV.

Compounds are evaluated against a GABA concentration that evokes <10% of the maximal evokable GABA current. Each oocyte is exposed to increasing concentrations of compound in order to evaluate a concentration/effect relationship. Compound efficacy is expressed as a percent-change in current amplitude: 100*((Ic/I)–1), where Ic is the GABA evoked current amplitude observed in the presence of compound and I is the GABA evoked current amplitude observed in the absence of compound.

Specificity of a compound for the Ro15-1788 site is determined following completion of the concentration/effect curve. After washing the oocyte sufficiently to remove previously applied compound, the oocyte is exposed to GABA+1 μM Ro15-1788, followed by exposure to GABA+1 μM Ro15-1788 + compound. Percent change due to addition of compound is calculated as described above. Any percent change observed in the presence of Ro15-1788 is subtracted from the percent changes in current amplitude observed in the absence of 1 μM Ro15-1788. These net values are used for the calculation of average efficacy and $EC_{50}$ values.

To evaluate average efficacy and $EC_{50}$ values, the concentration/effect data are averaged across cells and fit to the logistic equation. Average values are reported as mean ± standard error.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

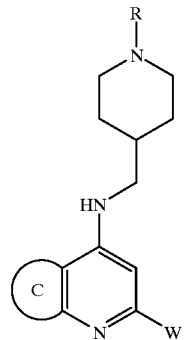

or a pharmaceutically acceptable non-toxic salt thereof wherein:

the C ring represents a thiophene, or a pyridine ring each of which is optionally substituted with one or two groups independently selected from a group consisting of $C_1$–$C_6$ alkyl, $C_1$–$C_6$ alkoxy, halogen, hydroxy, amino, mono- or di-($C_1$–$C_6$)alkylamino, and trifluoromethyl;

W is aryl, or heteroaryl; each of which is optionally mono or disubstituted independently with halogen, hydroxy, lower alkyl, lower alkoxy, amino, or mono- or dialkylamino where each alkyl portion is lower alkyl, or $CONR_4R_5$ wherein $R_4$ and $R_5$ are the same or different and represent lower alkyl; and R represents hydrogen, ($C_1$–$C_6$) alkyl, hydroxy ($C_1$–$C_6$) alkyl, amino($C_1$–$C_6$) alkyl, mono- or di($C_1$–$C_6$)alkyl, amino($C_1$–$C_6$) alkyl, alkoxy($C_1$–$C_6$) alkyl, ($C_1$–$C_6$)alkoxy, aryl($C_1$–$C_6$) alkyl; or $CONR_1R_2$ wherein $R_1$ and $R_2$ are the same or different and represent hydrogen or lower alkyl.

2. A compound according to claim 1 which is:

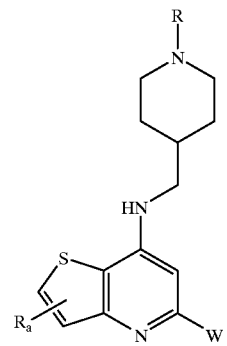

or a pharmaceutically acceptable non-toxic salt thereof wherein:

$R_a$ is hydrogen, $C_1$–$C_6$ alkoxy, $C_1$–$C_6$ alkoxy, halogen, hydroxy, amino, mono- or di($C_1$–$C_6$)alkyl amino, or trifluoromethyl;

R is hydrogen or lower alkyl; and

W is aryl, or heteroaryl; each of which may be mono or disubstituted independently with halogen, hydroxy, lower alkyl, lower alkoxy, amino, or mono- or dialkylamino where each alkyl portion is lower alkyl, or $CONR_4R_5$ wherein $R_4$ and $R_5$ are the same or different and represent lower alkyl.

3. A compound according to claim 1 which is:

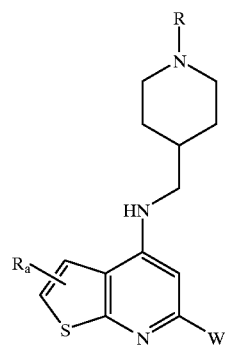

or a pharmaceutically acceptable non-toxic salt thereof wherein:

$R_a$ is hydrogen, $C_1$–$C_6$ alkoxy, $C_1$–$C_6$ alkoxy, halogen, hydroxy, amino, mono- or di($C_1$–$C_6$)alkyl amino, or trifluoromethyl R is hydrogen or lower alkyl; and W is aryl, or heteroaryl; each of which may be mono or disubstituted independently with halogen, hydroxy, lower alkyl, lower alkoxy, amino, or mono- or dialkylamino where each alkyl portion is lower alkyl.

4. A compound according to claim 1 which is:

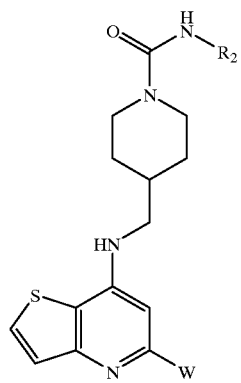

or a pharmaceutically acceptable non-toxic salt thereof wherein:

W is aryl, or heteroaryl; each of which may be mono or disubstituted independently with halogen, hydroxy, lower alkyl, lower alkoxy, amino, or mono- or dialkylamino where each alkyl portion is lower alkyl, or $CONR_4R_5$ wherein $R_4$ and R5 are the same or different and represent lower alkyl and $R_2$ represents hydrogen, or lower alkyl.

5. A compound of the formula:

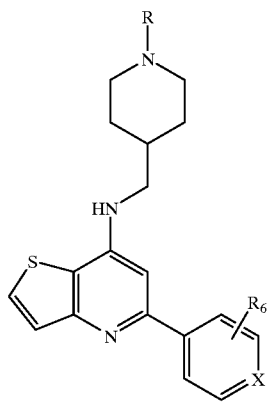

or a pharmaceutically acceptable non-toxic salt thereof wherein:

R is hydrogen, lower alkyl, hydroxyalkyl, aminoalkyl, alkoxyalkyl, lower alkoxy, or arylalkyl where each alkyl portion is lower alkyl, or $CONR_1R_2$ wherein $R_1$ and $R_2$ are the same or different and represent lower alkyl;

$R_6$ is halogen, hydroxy, lower alkyl, lower alkoxy, amino, mono- or dialkylamino where each alkyl portion is lower alkyl, or $CONR_4R_5$ wherein $R_4$ and $R_5$ are the same or different and represent lower alkyl; and X is nitrogen, or $CR_9$, wherein $R_9$ is hydrogen, alkyl, halogen, hydroxy, or lower alkoxy.

6. A compound of the formula:

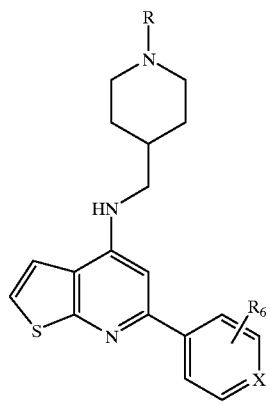

or the pharmaceutically acceptable non-toxic salts thereof wherein:

R is hydrogen, lower alkyl, hydroxyalkyl, aminoalkyl, alkoxyalkyl, lower alkoxy, arylalkyl where each alkyl portion is lower alkyl, or $CONR_1R_2$ wherein $R_1$ and $R_2$ are the same or different and represent lower alkyl;

$R_6$ is halogen, hydroxy, lower alkyl, lower alkoxy, amino, mono- or dialkylamino where each alkyl portion is lower alkyl, or $CONR_4R_5$ wherein $R_4$ and $R_5$ are the same or different and represents lower alkyl; and X is nitrogen, or $CR_9$ wherein $R_9$ is hydrogen, alkyl, halogen, hydroxy, or lower alkoxy.

7. A compound of the formula:

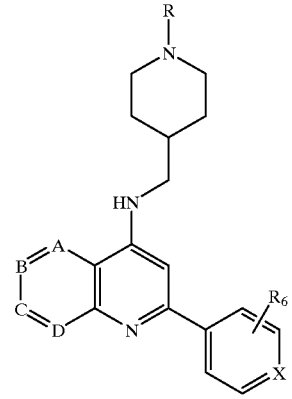

or a pharmaceutically acceptable non-toxic salt thereof wherein:

A, B, C, and D are $CR_3$ or nitrogen, provided that only one of A, B, C, or D is nitrogen;

$R_3$ is hydrogen, alkyl, halogen, hydroxy, or lower alkoxy;

R is hydrogen, lower alkyl, hydroxyalkyl, aminoalkyl, alkoxyalkyl, lower alkoxy, arylalkyl where each alkyl portion is lower alkyl, or $CONR_1R_2$ wherein $R_1$ and $R_2$ are the same or different and represent lower alkyl;

$R_6$ is halogen, hydroxy, lower alkyl, lower alkoxy, amino, mono- or dialkylamino where each alkyl portion is lower alkyl, or $CONR_4R_5$ wherein $R_4$ and $R_5$ are the same or different and represent lower alkyl; and X is $CR_9$ or nitrogen, where $R_9$ is hydrogen, lower alkyl, halogen, hydroxy, or lower alkoxy.

8. A compound according to claim 1 which is N-(4-piperidinylmethyl)-5-(4-fluorophenyl)thieno[3,2-b]pyridin-7-amine.

9. A compound according to claim 1 which is N-(4-piperidinylmethyl)-5-phenylthieno[3,2-b]pyridin-7-amine.

10. A compound according to claim 1 which is N-(4-piperidinylmethyl)-5-(3-methoxyphenyl)thieno[3,2-b]pyridin-7-amine.

11. A compound according to claim 1 which is N-(4-piperidinylmethyl)-5-(4-ethoxyphenyl)thieno[3,2-b]pyridin-7-amine.

12. A compound according to claim 1 which is N-(4-piperidinylmethyl)-5-(4-pyridinyl)thieno[3,2-b]pyridin-7-amine.

13. A compound according to claim 1 which is N-(4-piperidinylmethyl-N-ethylcarboxamide)-5-(4-fluorophenyl)thieno[3,2-b]pyridin-7-amine.

14. A compound according to claim 1 which is 8-(N-(piperidin-4-ylmethyl)amino)-2-phenyl-1,5-naphthyridine.

15. A compound according to claim 1 which is N-(4-piperidinylmethyl)-6-phenylthieno[2,3-b]pyridin-4-amine.

16. The compound according to claim 1 wherein the heteroaryl of W is 2- or 3-thienyl, or 2-, 3-, or 4- pyridyl.

17. The compound according to claim 2 wherein the heteroaryl of W is 2- or 3-thienyl, or 2-, 3-, or 4- pyridyl.

18. The compound according to claim 3 wherein the heteroaryl of W is 2- or 3-thienyl, or 2-, 3-, or 4- pyridyl.

19. The compound according to claim 4 wherein the heteroaryl of W is 2- or 3-thienyl, or 2-, 3-, or 4- pyridyl.

* * * * *